(12) United States Patent
McAdam et al.

(10) Patent No.: US 11,044,937 B2
(45) Date of Patent: Jun. 29, 2021

(54) SOLUTION COMPRISING NICOTINE IN UNPROTONATED FORM AND PROTONATED FORM

(71) Applicant: Nicoventures Holdings Limited, London (GB)

(72) Inventors: Kevin Gerard McAdam, London (GB); Connor Bruton, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 15/525,194

(22) PCT Filed: Nov. 6, 2015

(86) PCT No.: PCT/GB2015/053368
§ 371 (c)(1),
(2) Date: May 8, 2017

(87) PCT Pub. No.: WO2016/071705
PCT Pub. Date: May 12, 2016

(65) Prior Publication Data
US 2018/0279667 A1    Oct. 4, 2018

(30) Foreign Application Priority Data
Nov. 7, 2014 (GB) .................. 1419865

(51) Int. Cl.
| | | |
|---|---|---|
| *A24F 47/00* | (2020.01) | |
| *A24B 15/167* | (2020.01) | |
| *A61K 31/465* | (2006.01) | |
| *A61K 47/12* | (2006.01) | |
| *A61K 9/08* | (2006.01) | |
| *A24B 15/16* | (2020.01) | |
| *A61K 9/00* | (2006.01) | |
| *A24F 40/40* | (2020.01) | |
| *A24B 15/30* | (2006.01) | |
| *A61K 47/10* | (2017.01) | |
| *A24F 40/10* | (2020.01) | |

(52) U.S. Cl.
CPC ............ *A24B 15/167* (2016.11); *A24B 15/16* (2013.01); *A24B 15/301* (2013.01); *A24F 40/10* (2020.01); *A24F 40/40* (2020.01); *A61K 9/0073* (2013.01); *A61K 9/0078* (2013.01); *A61K 9/08* (2013.01); *A61K 31/465* (2013.01); *A61K 47/10* (2013.01); *A61K 47/12* (2013.01)

(58) Field of Classification Search
CPC .................................................. A24B 15/167
See application file for complete search history.

(56) References Cited

U.S. PATENT DOCUMENTS

| | | |
|---|---|---|
| 4,117,850 A | 10/1978 | Wood |
| 4,579,858 A | 4/1986 | Ferno et al. |
| 4,597,961 A | 7/1986 | Etscorn |
| 4,655,231 A * | 4/1987 | Ray .............. A61K 31/465 131/352 |
| 4,830,028 A | 5/1989 | Lawson |
| 4,924,888 A | 5/1990 | Perfetti |
| 5,031,646 A | 7/1991 | Lippiello |
| 5,626,866 A | 5/1997 | Ebert et al. |
| 6,799,576 B2 | 10/2004 | Farr |
| 7,726,320 B2 | 6/2010 | Robinson et al. |
| 8,079,371 B2 | 12/2011 | Robinson et al. |
| 8,156,944 B2 | 4/2012 | Han |
| 9,974,743 B2 | 5/2018 | Rose |
| 2002/0059939 A1 | 5/2002 | Fox |
| 2003/0176467 A1 | 9/2003 | Andersson |
| 2003/0192540 A1 | 10/2003 | Myrman |
| 2004/0198818 A1 | 10/2004 | Quallich et al. |
| 2004/0213744 A1 | 10/2004 | Lulla |
| 2004/0261487 A1 | 12/2004 | Chen |
| 2005/0009870 A1 | 1/2005 | Sher |
| 2006/0018840 A1 * | 1/2006 | Lechuga-Ballesteros ......... A01N 43/40 424/45 |
| 2006/0073182 A1 | 4/2006 | Wong |
| 2006/0196518 A1 | 9/2006 | Hon |
| 2006/0283468 A1 | 12/2006 | Lipowicz |
| 2007/0134169 A1 | 6/2007 | Rabinoff |
| 2007/0135461 A1 | 6/2007 | Rodgers |
| 2007/0267031 A1 | 11/2007 | Hon |
| 2007/0280972 A1 | 12/2007 | Zhang |
| 2008/0092912 A1 | 4/2008 | Robinson |
| 2008/0138423 A1 | 6/2008 | Gonda |

(Continued)

FOREIGN PATENT DOCUMENTS

| | | |
|---|---|---|
| AU | 2015341517 B2 | 1/2018 |
| CA | 2446102 | 4/2004 |

(Continued)

OTHER PUBLICATIONS

GB Search Report, Application No. GB1419865.9, dated May 7, 2015, 4 pages.
Written Opinion of International Preliminary Examining Authority, International Application No. PCT/GB2015/053368, dated Oct. 4, 2016, 7 pages.
International Preliminary Report on Patentability, International Application No. PCT/GB2015/053368, dated Feb. 3, 2017, 8 pages.
International Search Report and Written Opinion, PCT/GB2015/053368, dated Jan. 15, 2016, 12 pages.

(Continued)

*Primary Examiner* — Eric Yaary
(74) *Attorney, Agent, or Firm* — Patterson Thuente Pedersen, PA

(57) ABSTRACT

There is provided a nicotine solution, including a carrier; nicotine in unprotonated form and in protonated form; and one or more acids, wherein at least benzoic acid, levulinic acid or a mixture thereof is present; and wherein the total content of acid present in the solution is no greater than 0.6 mole equivalents based on the nicotine.

5 Claims, 1 Drawing Sheet

(56) References Cited

U.S. PATENT DOCUMENTS

| | | |
|---|---|---|
| 2008/0228214 A1 | 9/2008 | Hoan et al. |
| 2008/0302375 A1 | 12/2008 | Andersson et al. |
| 2009/0023819 A1 | 1/2009 | Axelsson |
| 2009/0095311 A1 | 4/2009 | Han |
| 2010/0116691 A1 | 5/2010 | Papadimitrakopoulos |
| 2010/0260688 A1 | 10/2010 | Warchol |
| 2011/0168194 A1 | 7/2011 | Hon |
| 2011/0226236 A1* | 9/2011 | Buchberger ......... A61M 11/041 128/200.23 |
| 2011/0268809 A1 | 11/2011 | Brinkley |
| 2011/0274628 A1 | 11/2011 | Borschke |
| 2012/0255567 A1 | 10/2012 | Rose et al. |
| 2013/0081623 A1* | 4/2013 | Buchberger ......... A61M 11/041 128/203.27 |
| 2013/0081642 A1 | 4/2013 | Safari |
| 2013/0298905 A1 | 11/2013 | Levin |
| 2014/0018840 A1 | 1/2014 | Morgan et al. |
| 2014/0060554 A1 | 3/2014 | Collett |
| 2014/0166027 A1 | 6/2014 | Fuisz et al. |
| 2014/0253144 A1 | 9/2014 | Novak |
| 2014/0261486 A1 | 9/2014 | Potter et al. |
| 2014/0261487 A1 | 9/2014 | Chapman et al. |
| 2014/0261489 A1 | 9/2014 | Cadieux et al. |
| 2014/0261493 A1 | 9/2014 | Smith |
| 2014/0283825 A1 | 9/2014 | Buchberger |
| 2014/0299125 A1 | 10/2014 | Buchberger |
| 2014/0345635 A1* | 11/2014 | Rabinowitz ............ A24B 15/16 131/352 |
| 2015/0020823 A1 | 1/2015 | Lipowciz |
| 2015/0250232 A1 | 9/2015 | Hon |
| 2015/0313275 A1* | 11/2015 | Anderson ............... A24B 15/10 131/352 |
| 2017/0215476 A1 | 8/2017 | Dickens et al. |

FOREIGN PATENT DOCUMENTS

| | | |
|---|---|---|
| CN | 86103434 A | 11/1986 |
| CN | 1102647 A | 5/1995 |
| CN | 1607950 A | 4/2005 |
| CN | 2777995 Y | 5/2006 |
| CN | 201067079 Y | 6/2008 |
| CN | 201079011 Y | 7/2008 |
| CN | 101437496 A | 5/2009 |
| CN | 101951796 A | 1/2011 |
| DE | 29803260 U1 | 7/1998 |
| EP | 0283672 A2 | 9/1988 |
| EP | 0289342 A2 | 11/1988 |
| EP | 0290911 A2 | 11/1988 |
| EP | 0520231 A2 | 12/1992 |
| EP | 1 509 227 B1 | 3/2005 |
| EP | 1618803 | 1/2006 |
| EP | 1618803 A1 | 1/2006 |
| EP | 2022349 A1 | 2/2009 |
| EP | 2022350 A1 | 2/2009 |
| EP | 2779786 A1 | 9/2014 |
| EP | 2993999 A1 | 3/2016 |
| EP | 3145348 A1 | 3/2017 |
| EP | 3214957 B1 | 2/2019 |
| GB | 2133691 A | 8/1984 |
| IN | 0351/KOL/2006 A | 7/2007 |
| JP | 559135878 A | 8/1984 |
| JP | 2003024036 A | 1/2003 |
| JP | 2004512907 A | 4/2004 |
| JP | 2012223190 A | 11/2012 |
| JP | 2013521075 A | 6/2013 |
| JP | 2014516624 A | 7/2014 |
| KR | 20120104183 A | 9/2012 |
| RU | 2333014 C2 | 9/2008 |
| WO | WO9503050 A2 | 2/1995 |
| WO | WO2000122907 A1 | 4/2001 |
| WO | WO 2003/101454 A1 | 12/2003 |
| WO | WO2004029050 A1 | 4/2004 |
| WO | WO 2004076289 | 9/2004 |
| WO | WO2004076289 A2 | 9/2004 |
| WO | WO2004076412 A2 | 9/2004 |
| WO | WO2005004989 A2 | 1/2005 |
| WO | WO2005039531 A1 | 5/2005 |
| WO | WO2005075452 A1 | 8/2005 |
| WO | WO2005089728 A2 | 9/2005 |
| WO | WO2005108389 | 11/2005 |
| WO | WO 2006/004646 A1 | 1/2006 |
| WO | WO2006008108 A2 | 1/2006 |
| WO | WO2006034833 A1 | 4/2006 |
| WO | WO2006073366 A1 | 7/2006 |
| WO | WO2007002597 A2 | 1/2007 |
| WO | WO2007038215 A1 | 4/2007 |
| WO | WO2008073942 A2 | 6/2008 |
| WO | WO-2009001085 A1 | 12/2008 |
| WO | WO2009007767 A1 | 1/2009 |
| WO | WO2009007768 A1 | 1/2009 |
| WO | WO2009007769 A1 | 1/2009 |
| WO | WO2009007770 A1 | 1/2009 |
| WO | WO2009007771 A1 | 1/2009 |
| WO | WO-2009079641 A2 | 6/2009 |
| WO | WO-2011034723 A1 | 3/2011 |
| WO | WO2011045609 A1 | 4/2011 |
| WO | WO2011109849 | 9/2011 |
| WO | WO2011139684 | 11/2011 |
| WO | WO2011139811 | 11/2011 |
| WO | WO2012110819 | 8/2012 |
| WO | WO2012134380 | 10/2012 |
| WO | WO-2012142293 A2 | 10/2012 |
| WO | WO-2013116558 A1 | 8/2013 |
| WO | WO-2013116561 A1 | 8/2013 |
| WO | WO-2014004648 A1 | 1/2014 |
| WO | WO-2014150245 A1 | 9/2014 |
| WO | WO-2014151434 A2 | 9/2014 |
| WO | WO2014159250 A1 | 10/2014 |
| WO | WO 2014/182736 A1 | 11/2014 |
| WO | WO-2014177859 A1 | 11/2014 |
| WO | WO 2015/009862 A2 | 1/2015 |
| WO | WO 2015054885 A1 | 4/2015 |
| WO | WO 2015/084544 | 6/2015 |
| WO | WO-2015091258 A1 | 6/2015 |
| WO | WO-2015179292 A1 | 11/2015 |
| WO | WO-2015189623 A1 | 12/2015 |
| WO | WO2016071705 A1 | 5/2016 |

OTHER PUBLICATIONS

Villégier AS, Blanc G, Glowinski J, Tassin JP (Sep. 2003). "Transient behavioral sensitization to nicotine becomes long-lasting with monoamine oxidases inhibitors". Pharmacol. Biochem. Behav. 76 (2): 267-74. doi:10.1016/S0091-3057(03)00223-5. PMID 14592678.

Amsterdam, J. V.; Talhout, R.; Vleeming, W.; Opperhuizen, A. (2006). "Contribution of monoamine oxidase (MAO) inhibition to tobacco and alcohol addiction". Life Sciences 79 (21): 1969-1973. doi:10.1016/j.lfs.2006.06.010. PMID 16884739.

Poindexter, E.H. Jr, Carpenter, R.D. 1962. "The isolation of harmane and norharmane from tobacco and cigarette smoke." Phytochemistry, 1(3): 215-221.

Berlin, I.; m. Anthenelli, R. (2001). "Monoamine oxidases and tobacco smoking". The International Journal of Neuropsychopharmacology 4 (1): 33-42. doi:10.1017/S1461145701002188. PMID 11343627.

Fowler, J. S.; Volkow, N. D.; Wang, G. J.; Pappas, N.; Logan, J.; Shea, C.; Alexoff, D.; MacGregor, R. R.; Schlyer, D. J.; Zezulkova, I.; Wolf, A. P. (1996). "Brain monoamine oxidase in cigarette smokers". Proceedings of the National Academy of Sciences of the United States of America 93 (24): 14065-14069. doi:10.1073/pnas.93.24.14065. PMC 19495. PMID 8943061.

Fowler, J. S.; Volkow, N. D.; Wang, G.-J.; Pappas, N.; Logan, J.; MacGregor, R.; Alexoff, D.; Shea, C.; Schlyer, D.; Wolf, A. P.; Warner, D.; Zezulkova, I.; Cilento, R. (1996). "Inhibition of monoamine oxidase B in the brains of smokers". Nature 379 (6567): 733-736. doi:10.1038/379733a0. ISSN 0028-0836. PMID 8602220.

Zhang, L., Ashley, D. L., Watson, C. H., Quantitative Analysis of Six Heterocyclic Aromatic Amines in Mainstream Cigarette Smoke Condensate Using Isotope Dilution Liquid Chromatography-Electrospray Ionization Tandem Mass Spectrometry, Nicotine & Tobacco Research (2010) vol. 13, No. 2, pp. 120-126 doi: 10.1093/ntr/ntq219.

(56) References Cited

OTHER PUBLICATIONS

Clayton P M et al., Spectroscopic investigations into the acid-base properties of nicotine at different temperatures, Anal. Methods, 2013, 5, pp. 81-88.
Clayton P M et al., Use of chiroptical spectroscopy to determine the ionisation status of (S)-niotine in e-cigarette formulations and snus, ST49, CORESTA Congress, Quebec City, Canad, Oct. 12-16, 2014. Available at: http://www.bat-science.com/groupms/sites/BAT_9GVJXS.nsf/vwPagesWebLive/DO9PVC3G/$FiLE/CORESTA_PC_2014.pdf.
Chinese Search Report and Office Action, Application No. 201580061121.X, dated Jan. 23, 2018, 9 pages.
Japanese Decision to Grant, Application No. 2017-523309, dated Jul. 24, 2018, 3 pages (6 pages with translation.).
Epperson C N et al., Sex, GABA, and nicotine: the impact of smoking on cortical GABA levels across the menstrual cycle as measured with proton magnetic resonance spectroscopy, Biol Psychiatry, Jan. 1, 2005, vol. 57, No. 1, pp. 44-48.
Application and File History for U.S. Appl. No. 15/525,163, filed May 8, 2017, Inventors: McAdam et al.
Application and File History for U.S. Appl. No. 15/764, 612, filed Mar. 29, 2018, Inventors: McAdam et al.
Mil-G-45204 Military Specification: Gold Plating, Electrodeposited (Jun. 7, 1983) [S/S by MIL-DTL-45204D], 18 pages dated Jun. 7, 1983.
ASTM, *Standard Specification for Electrodeposited Coatings of Gold for Engineering Uses*, B488-11 (2011), 6 pages.
SAE, *AMS 2422F Plating, Gold*, Feb. 6, 2014, 2 pages.
QQ-S-365D Federal Specification: Silver Plating, Electrodeposited, General Requirements for (Jun. 3, 1985), 12 pages.
ASTM, *B700-8 Standard Specification for Electrodeposited Coatings of Silver for Engineering Use*, (2014), 5 pages.
SAE, *AMS 2410K Plating, Silver, Nickel Strike, High Bake*, Apr. 19, 2010, 4 pages.
SAE, *AMS 2411H Plating, Silver, for High Temperature Applications*, Dec. 17, 2013, 4 pages.
SAE, *AMS 2412K Plating, Silver, Copper Strike, Low Bake*, Jan. 26, 2015, 4 pages.
Vapegrl, *Silver and Gold E-cigarettes*, vapegrl.com, Available from: http://vapegrl.com/silver-gold-e-cigarettes/, as accessed on Feb. 15, 2016, 8 pages.
Vaperanks, *Luxury Customization Company Launches 24ct-Gold-Plated E-Cigarettes*, vaperanks.com, as available from: http://vaperanks.com/luxury-customization-company-launches-24ct-gold-plated-e-cigarette/, as accessed on Feb. 4, 2016, 3 pages.
Fox, Lindsay, *10 Coolest E-Cig Mods*, ecigarettes reviewed, Jul. 9, 2013 as available from http://ecigarettereviewed.com/coolest-e-cigs-mods and retrieved Nov. 15, 2016, 18 pages.
International Search Report and Written Opinion, Application No. PCT/GB2016/053051, dated Jan. 2, 2017, 13 pages.
Written Opinion, Application No. PCT/GB2016/053051, dated Aug. 16, 2017, 7 pages.
Great Britain Search Report, Application No. GB1517361.0, dated Feb. 8, 2016, 5 pages.
Great Britain Search Report, Application No. GB1419865.9, dated May 7, 2015, 4 pages.
Britton M et al., Impact of health technology assessments, some experiences of SBU, Int J Technol Assess Health Care, Fall 2002, vol. 18 No. 4 pp. 824-831.
Chakraborty S, Mediated electrocatalytic oxidation of bioanalytes and biosensing of glutamate using functionalized multiwall carbon nanotubes-biopolymer nanocomposite, Journal of Electroanalytical Chemistry, Nov. 1, 2007, vol. 609, No. 2, pp. 155-162.
Cymes G D, The unanticipated complexity of the selectivity-filter glutamates of nicotinic receptors, Nature Chemical Biology, Dec. 2012, vol. 8, No. 12, pp. 975-981.
Dankwa E et al., Aids to smoking cessation, New Zealand Medical Journal, Apr. 11, 1997, vol. 110, No. 1041 pp. 131-132.

Durazzo T C, Chronic cigarette smoking in alcohol dependence: associations with cortical thickness and N-acetylasparate levels in the extended brain reward system, Addict Biology, Mar. 2013, vol. 18, No. 2, pp. 379-391.
Giannos S A, Temporally controlled drug-delivery systems—coupling of pH oscillators with membrane-diffusion, Journal of Pharmaceutical Sciences, May 1995, vol. 84, No. 5, pp. 539-543.
Glueck C J, Nonpharmacologic and pharmacologic alternation of high-density lipoprotein cholesterol: therapeutic approaches to prevention of atheroschlerosis, Am Heart Journal, Nov. 1985, vol. 110, No. 5, pp. 1107-1115.
International Preliminary Report on Patentability, International Application No. PCT/GB2015/053369, dated Oct. 7, 2016, 7 pages.
International Search Report and Written Opinion, International Application No. PCT/GB2015/053369, dated Feb. 5, 2016, 9 pages.
Kalantari-Dehaghi M et al., Mechanisms of mitochondrial damage in keratinocytes by pemphigus vulgaris antibodies, Journal of Biological Chemistry, Jun. 7, 2013, vol. 288, No. 23, pp. 16916-16925.
Kovacic P et al., Iminium metabolite mechanism of nicotine toxicity and addiction: oxidative stress and electron transfer, Medical Hypotheses, 2005, vol. 64, No. 1, pp. 104-111.
Li D M, Catalytic Mechanism of Cytochrome P450 for 5'-Hydroxylation of nicotine: fundamentl reaction pathways and stereoselectivity, Journal of American Chemical Society, May 18, 2011, vol. 133, No. 19, pp. 7416-7427.
Mashhoon T et al., Anterior cingulate proton spectorscopy glumate levels differ as a function of smoking cessation outcome, Prog Neuropsychoparmacol Biol Psychiatry, Aug. 15, 2011, vol. 35, No. 7, p. 1709-1713.
Newton G D et al., New OTC drugs and devices 2002, a selective review, J Am Pharm Assoc, Mar.-Apr. 2004, vol. 44, No. 2, p. 211-225.
O'Neill J et al., Thalamic glutamate decreases with cigarette smoking, Psychopharmacology, (Berlin), Feb. 18, 2014, Epub ahead of print)—Jul. 2014 231(13) pp. 2717-2724.
Pankow J F, Conversion of nicotine in tobacco smoke to its volatile and available free-base form through the action of gaseous ammonia, Environmental Science & Technology, Aug. 1997, vol. 31 No. 8, p. 2428-2433.
Pankow J F, Percent free base nicotine in the tobacco smoke particulate matter of selected commercial and reference cigarettes, Chemical Research in Toxicology, Aug. 2003, vol. 16, No. 8, pp. 1014-1018.
Patel S U, Structural studies of Impatiens balsamina antimicrobial protein (Ib-AMP1), Biochemistry, Jan. 27, 1998, vol. 37, No. 4, pp. 983-990.
Petrov E G et al., Two-electron transfer reactions in proteins: bridge-mediated and proton-assisted processes, Phys Rev E Stat Nonlin Soft Matter Phys, Dec. 2003, vol. 68, part 1, 061916, epub Dec. 31, 2003.
Pinggera G M, Urinary acetonitrile concentrations correlate with recent smoking behaviour, BJU International vol. 95, No. 3, p. 306-309.
Pongjanyakul T and Kanjanabat S (2012) AAPS PharmSciTech 13(2): 674-685. Influence of pH modifiers and HPMC viscosity grates on nicotine-magnesium aluminium silicate complex loaded buccal matrix tablets.
Pongjanyakul T and Suksri H (2009) Colloids and Surfaces B: Biointerfaces 74: 103-113. Alginate-magnesium aluminium silicate films for buccal delivery of nicotine.
Sami P, Studies on electron transfer reactions of Keggin-type mixed addenda heteropolytungstovanadophosphates with NADH, Journal of Chemical Sciences, Mar. 2009, vol. 121, No. 2, pp. 155-161.
Vlachou S et al., Both GABA(B) receptor activation and blockage exacerbated anhedonic aspects of nicotine withdrawal in rats, Eur J Pharmacol., Mar. 25, 2011, vol. 655, No. 1-3, pp. 52-58.
Morie G P, Fractions of protonate and unprotonated nicotine in tobacco smoke at various pH, Tobacco Science, 167 (1972) 56 (ISSN: 0082-4623).
Armitage A K, D K Turner, Absorption of nicotine in cigarette and cigar smoke through the oral mucosa, Nature, 226 (1970) pp. 1231-1233.

(56) References Cited

OTHER PUBLICATIONS

Federal Register, Federal Register Doc .99/7022, Mar. 23, 1999, 14,086-14,096.
Great Britain Search Report, Application No. GB1419866.7, dated May 7, 2015, 4 pages.
Chinese Office Action, Application No. 201580060720.X, dated Dec. 4, 2017, 17 pages (35 pages with translation).
Japanese Office Action, Application No. 2017-523310, dated Apr. 10, 2018, 2 pages (5 pages with translation).
Chilean Office Action, Application No. 201701137, dated Aug. 20, 2018.
Korean Office Action, Application No. 10-2017-7012228, dated Oct. 22, 2018, 7 pages.
English Translation of Japanese Search Report, Application No. 2017-523310, dated Jan. 23, 2018, 8 pages.
Korean Office Action, Application No. 10-2017-7012229, dated Oct. 22, 2018, 12 pages (22 pages with translation).
Russian Office Action, Application No. 2018111280, dated Dec. 10, 2018, 8 pages.
Korean Notice of Allowance, Application No. 10-2017-701228, dated Apr. 28, 2019, 4 pages.
Chinese Office Action and Search Report, Chinese Application No. 201810383324.6, dated Jun. 3, 2020, 21 pages.
Abstract of Keithl Y L. et al., Industry research on the use and effects of levulinic acid: a case study in cigarette additives., Nicotine Tobacco Research, Oct. 2005, vol. 7(5), pp. 761-771.
Anonymous, "eGo-C User Manual Changeable System", Shenzhen Joyetech Co. Ltd, 17 pages, first cited in the Opposition to European Patent No. EP3214957, dated Nov. 13, 2019.
Anonymous, "The eRoll User Manual", Shenzhen Joyetech Co. Ltd, 9 pages, first cited in the Opposition to European Patent No. EP3214957, dated Nov. 13, 2019.
Application and File History for U.S. Appl. No. 15/525,194, filed May 8, 2017, inventor: Mcadam et al. 563 pages.
Barr P., "Technical Anaylsis of Joyetech eRoll cartridge and Joyetech eGo-C cartridge," Nov. 12, 2019, 3 pages.
Barsanti K C et al., Tobacco smoke particulate matter chemistry by NMR, Magnetic Resonance in Chemistry, 2007, vol. 45, pp. 167-170.
Bringing attention to e-cigarette pH as in important element for research and regulation, Tobacco Control, vol. 24 No. 4, May 14, 2014, 2 pages.
C. Maier, Polypropylene: The Definitive User'S Guide and Databook, Elsevier, (19980000), pp. 122-124, XP055656080, first cited in the Opposition to European Patent No. EP3214957, dated Nov. 13, 2019.
Certified Priority document of WO2015091258, Priority No. EP13198390.0, Priority date: Nov. 12, 2013, 26 pages.
Communication pursuant to Article 94(3) EPC for Application No. 16777777.0, dated Jun. 15, 2020, 9 pages.
"Consolidated list of citations—EP3214957," Nov. 19, 2019, 4 pages.
CRC Handbook of Chemistry and Physics 1989-1990.
"Declaration of John McKeon," European Patent Application No. 15794254.1 (EP3214957B), Opposition: Nerudia Limited, Nov. 12, 2019, 1 page.
"Declaration of Joseph P. Hamilton," Hamilton Declaration, Nov. 8, 2019, 7 pages.
Declaration of Marc Doring, Nov. 12, 2019, 10 pages.
"Declaration of Sara Luisa Mellor de Sousa," European Patent Application No. 15794254.1 (EP3214957B), Opposition: Nerudia Limited, Nov. 11, 2019, 1 page.
Duell A Ketal., Free-base Nicotine Determination in Electronic Cigarette Liquids by 1H NMR Spectroscopy, Chemical Research in Toxicology, 2018, vol. 31, pp. 431-434.
El-Hellani A et al., Quantification of free-base and protonated nicotine in electronic cigarette liquids and aerosol emissions, Chemical Research in Toxicology, Aug. 17, 2015, vol. 28(8) pp. 1532-1537.

European Commission Directorate-General for Health & Consumers, Scientific Committee on Emerging and Newly Identified Health Risks, SCENIHR, Addictiveness and Attractiveness of Tobacco Additives, written procedure, Jul. 6, 2010, 112 pages.
European Patent Office Boards of Appeal Datasheet for the Decision for T405/13, Application No. 03077709.8, Apr. 9, 2014, 15 pages.
Ev STOCKEL, Technical Report, Nov. 8, 2019, 3 pages.
Ev STOCKEL, Technical Report on Absorption Behaviour of Protonated Nicotine, Jul. 9, 2020, 5 pages.
Extended European Search Report for Application No. 20183945.3, dated Oct. 13, 2020, 8 pages.
Extended European Search Report for European Application No. 18212381.0, dated Apr. 15, 2019, 6 pages.
Extraction from the Register of European Patents of WO2015091258 downloaded Dec. 11, 2019, 1 pages.
Goldgenie, "A 24 carat gold-plated electronic cigarette E-cigarette reviews and rankings," Feb. 17, 2014, 6 pages.
Henningfield J.E. et al., "Estimation of available nicotine content of six smokeless tobacco products," Tobacco Control, vol. 4, 1995, pp. 57-61.
International Preliminary Report on Patentability for Appl. No. PCT/GB2016/053051, dated Nov. 27, 2017, 7 pages.
Joyetech, "The eRoll—User Manual," published online on Oct. 5, 2012, 9 pages.
Joytech, "eRoll Starter Kit," eRoll series, E-Cigarette, Printout Wayback Machine for the webpage http://www.joyetech.com/product/details.php?gno-123, Oct. 26, 2014, 4 pages.
Leffingwell, "Leaf Chemistry BA Basic Constituents of Tobacco Leaf and Differences among Tobacco Types", Blackwell Science (Pub), Jan. 1, 1999) XP055326787. Retrieved from the Internet: URL: http: www.leffingwell.com/download/Leffingwell—Tobacco production chemistry and technology.pdf.
Matt Richtel, The £-Cigarette Industry, Waiting to Exhale (New York Times, dated Oct. 26, 2013), 8 pages.
Notice of Allowance for Korean Application No. 10-2017-7012228, dated Apr. 28, 2019, 3 pages (4 pages with translation).
Notice of Opposition to EP3214957 B1, filed by George W. Schlich, dated Nov. 13, 2019, 23 pages.
Notice of Opposition to EP3214957, filed by Plate Schweitzer Zounek, dated Nov. 13, 2019, 42 pages.
Notification of First Office Action for Chinese Application No. 2018103833246, dated Jun. 3, 2020, 21 pages.
Occupational Health Guideline for Nicotine, U.S. Department of Labor, Occupational Safety and Health Administration, Sep. 1978, 6 pages.
Office Action dated Aug. 20, 2018 for Chilean Application No. 201701108, 11 pages.
Office Action dated Aug. 5, 2020 for European Application No. 15794254.1, 138 pages.
Opposition to EP3214957, filed by JT International, Bandpay & Greuter, Nov. 13, 2019, 20 pages.
Opposition to EP3214957, filed by Nerudia Limited, Newburn Ellis, Nov. 13, 2019, 29 pages.
Perfetti T A, Structural Study of Nicotine Salts, Beitrage zur Tabakforschung International, Jun. 1983, vol. 12, No. 2, pp. 43-54.
Picture of the atomizer of the "Wick of the eRoll E-Cigarette," Nov. 10, 2019, 2 pages.
"Report on determining the cartridge material of the eRoll E-Cigarette," Analysis of an eRoll cartridge, Annex D4c, Nov. 10, 2019, 3 pages.
Sastri V.R., "Plastics in Medical Devices: Properties, Requirements and Applications," 2010, pp. 100,226,230.
Screenshot of "Joyetech eRoll Manual," Retreived from the Internet: URL: https://www.joyetech.com/download/?mid=1145, Oct. 5, 2012, 1 page.
Screenshot of the image gallery of the "6th Global Forum on Nicotine," Retrieved from the Internet: URL: https://gfn.net.co/archive/2014-photo-galleries/2014-g2/category/3-gfn2014-g2?start=0, 1 page, first cited in the Opposition Against European Patent No. EP 321495761, Nov. 13, 2019.
Search Report dated Jan. 21, 2020 for Chinese Application No. 201680056890.5, 2 pages.

(56) References Cited

OTHER PUBLICATIONS

Seeman et al., The Form of Nicotine in Tobacco. Thermal Transfer of Nicotine and Nicotine Acid Salts to Nicotine in the Gas Phase, in J Agric Food Chern, 1999, vol. 47, pp. 5133-5145.
"The Vapor Pro" archived Feb. 23, 2014 and available at URL: https://web.archive.org/web/20140223102416/http://www.thevaporpro.com/faq.html.
Thermo Fisher Scientific, Measuring pH of Non-Aqueous and Mixed Samples, Application Note 007, 2014, document reference AN-PHNONAQS-E 1014 Rev A, 4 pages.
Tripathi D., "Practical Guide to Polypropylene," Rapra Technology Ltd, 2002, pp. 58,59,98,99.
Vas C A et al., "Acetoin is a precursor to diacetyl in e-cigarette liquids," Food and Chemical Toxicology, 2019, vol. 133, 110727, 16 pages.
Wikipedia entry for Lik Hon, https:/ /en.wikipedia.org/wiki/Hon Lik, downloaded Oct. 18, 2019, 4 pages.

\* cited by examiner

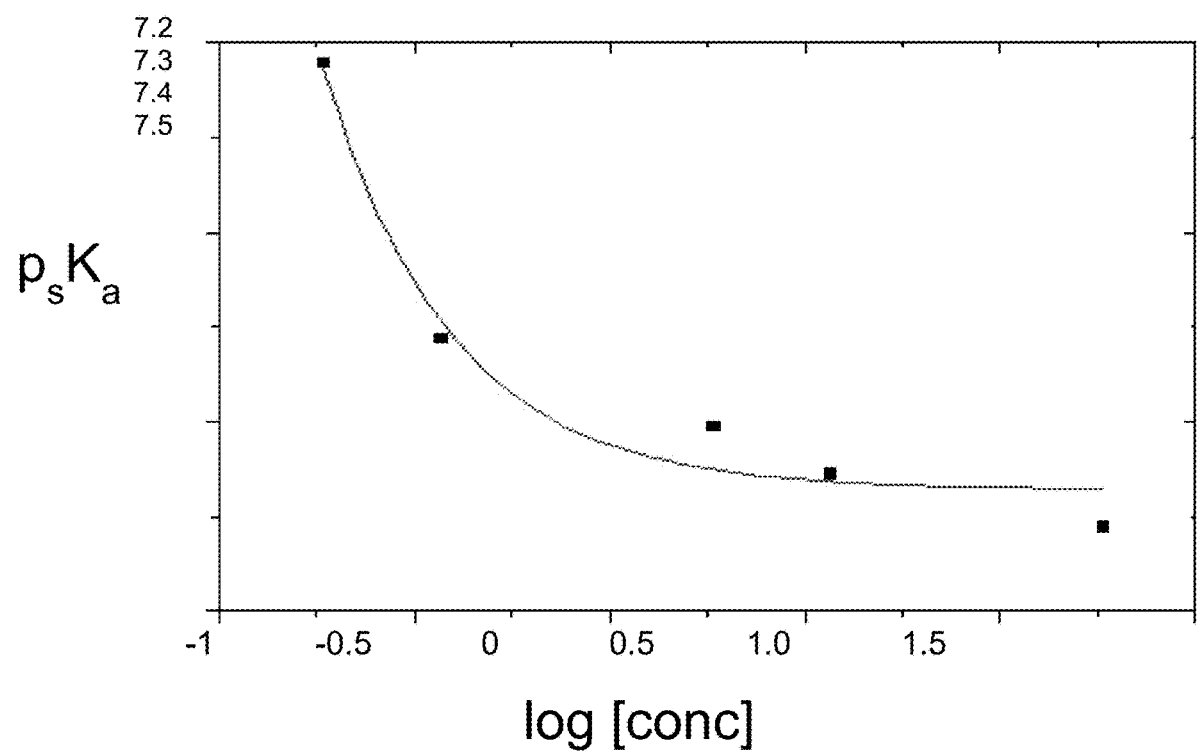

SOLUTION COMPRISING NICOTINE IN UNPROTONATED FORM AND PROTONATED FORM

CROSS-REFERENCE TO RELATED APPLICATIONS

The present application is a National Phase entry of PCT Application No. PCT/GB2015/053368, filed Nov. 6, 2015, which claims priority from GB Patent Application No. 1419865.9, filed Nov. 7, 2014, each of which is hereby fully incorporated herein by reference in its entirety.

TECHNICAL FIELD

The present disclosure relates to a nicotine solution, containers in which are contained the nicotine solution and to electronic vapor provision systems such as electronic nicotine delivery systems (e.g. e-cigarettes) incorporating said solution.

BACKGROUND

Electronic vapor provision systems such as e-cigarettes generally contain a reservoir of liquid which is to be vaporized, typically containing nicotine. When a user inhales on the device, a heater is activated to vaporize a small amount of liquid, which is therefore inhaled by the user.

The use of e-cigarettes in the UK has grown rapidly, and it has been estimated that there are now over a million people using them in the UK.

One challenge faced in providing such systems is to provide from the vapor provision device a vapor to be inhaled which provides consumers with an acceptable experience.

Some consumers may prefer an e-cigarette that generates an aerosol that closely 'mimics' smoke inhaled from a tobacco product such as a cigarette. Aerosols from e-cigarettes and smoke from tobacco products such as cigarettes provides to the user a complex chain of flavor in the mouth, nicotine absorption in the mouth and throat, followed by nicotine absorption in the lungs. These various aspects are described by users in terms of flavor, intensity/quality, impact, irritation/smoothness and nicotine reward. Nicotine contributes to a number of these factors, and is strongly associated with factors such as impact, irritation and smoothness; these are readily perceived by consumers, and e-cigarettes may offer too much or too little of these parameters for consumers, depending upon individual preferences. Nicotine reward is particularly complex as it results from both the amount of and speed with which nicotine is absorbed from the lining of the mouth, this is typically nicotine in the vapor phase, and from the amount and speed nicotine that is absorbed from the lungs, this is typically nicotine in the particulate phase of the aerosol which is inhaled. Each of these factors, and their balance, can strongly contribute to consumer acceptability of an e-cigarette. Providing means to optimize the overall vaping experience is therefore desirable to e-cigarette manufacturers.

SUMMARY

In one aspect there is provided a nicotine solution comprising: (i) a carrier; (ii) nicotine in unprotonated and in protonated form; and (iii) one or more acids, wherein at least benzoic acid, levulinic acid or a mixture thereof is present; and wherein the total content of acid present in the solution is no greater than 0.6 mole equivalents based on the nicotine.

In one aspect there is provided a contained nicotine solution comprising: (a) a container; and (b) a nicotine solution, comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine. In one aspect there is provided an electronic vapor provision system comprising: a vaporizer for vaporizing liquid for inhalation by a user of the electronic vapor provision system; a power supply comprising a cell or battery for supplying power to the vaporizer a nicotine solution, comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine.

In one aspect there is provided a process for improving the sensory properties of a vaporized nicotine solution, the process comprising: (a) providing a nicotine solution comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine; (b) vaporizing the nicotine solution.

In one aspect there is provided use of one or more acids for improving sensory properties of a vaporized nicotine solution, wherein the nicotine solution comprises: (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine.

DETAILED DESCRIPTION

As discussed herein the present disclosure provides a nicotine solution comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine.

We have found that by protonating some and only some of the nicotine present in a solution, such that the solution contains nicotine in unprotonated form and nicotine in protonated form, the solution when vaporized and inhaled provides desirable properties of flavor, impact, irritation, smoothness and/or nicotine reward for the user. We have particularly found that the levels of acid addition required by the present invention, namely wherein the total content of acid present in the solution is no greater than 0.6 mole equivalents based on the nicotine, may be used across a broad range of nicotine content solutions. At the levels of acid addition required by the present disclosure solutions may be provided having desirable properties of flavor, impact, irritation, smoothness and/or nicotine reward for the user both when the nicotine content is relatively low, such as 1.8 wt % nicotine or less and when the nicotine content is relatively high, such as greater than 1.8 wt % nicotine.

As is understood by one skilled in the art, nicotine may exist in unprotonated form, monoprotonated form or diprotonated form. The structures of each of these forms are given below.

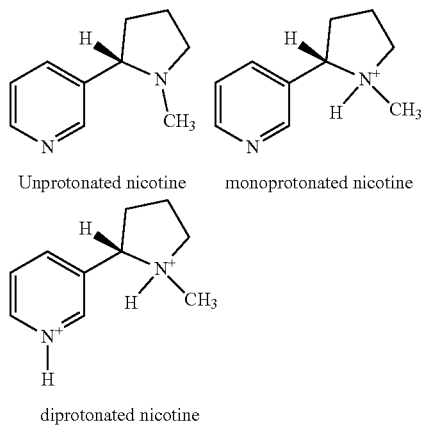

Unprotonated nicotine    monoprotonated nicotine diprotonated nicotine

Reference in the specification to protonated form means both monoprotonated nicotine and diprotonated nicotine. Reference in the specification to amounts in the protonated form means the combined amount of monoprotonated nicotine and diprotonated nicotine. Furthermore, when reference is made to a fully protonated formulation it will be understood that at any one time there may be very minor amounts of unprotonated nicotine present, e.g. less than 1% unprotonated.

For ease of reference, these and further aspects of the present disclosure are now discussed under appropriate section headings. However, the teachings under each section are not necessarily limited to each particular section.

The carrier of the nicotine solution may be any suitable solvent such that the nicotine solution can be vaporized for use. In one aspect the solvent is selected from glycerol, propylene glycol and mixtures thereof. In one aspect the solvent is at least glycerol. In one aspect the solvent consists essentially of glycerol. In one aspect the solvent consists of glycerol. In one aspect the solvent is at least propylene glycol. In one aspect the solvent consists essentially of propylene glycol. In one aspect the solvent consists of propylene glycol. In one aspect the solvent is at least a mixture of propylene glycol and glycerol. In one aspect the solvent consists essentially of a mixture of propylene glycol and glycerol. In one aspect the solvent consists of a mixture of propylene glycol and glycerol.

The carrier of the nicotine solution may be present in any suitable amount. In one aspect the carrier is present in an amount of 1 to 98 wt % based on the solution. In one aspect the carrier is present in an amount of 5 to 98 wt % based on the solution. In one aspect the carrier is present in an amount of 10 to 98 wt % based on the solution. In one aspect the carrier is present in an amount of 20 to 98 wt % based on the solution. In one aspect the carrier is present in an amount of 30 to 98 wt % based on the solution. In one aspect the carrier is present in an amount of 40 to 98 wt % based on the solution. In one aspect the carrier is present in an amount of 50 to 98 wt % based on the solution. In one aspect the carrier is present in an amount of 60 to 98 wt % based on the solution. In one aspect the carrier is present in an amount of 70 to 98 wt % based on the solution. In one aspect the carrier is present in an amount of 80 to 98 wt % based on the solution. In one aspect the carrier is present in an amount of 90 to 98 wt % based on the solution. In one aspect the carrier is present in an amount of 1 to 90 wt % based on the solution. In one aspect the carrier is present in an amount of 5 to 90 wt % based on the solution. In one aspect the carrier is present in an amount of 10 to 90 wt % based on the solution. In one aspect the carrier is present in an amount of 20 to 90 wt % based on the solution. In one aspect the carrier is present in an amount of 30 to 90 wt % based on the solution. In one aspect the carrier is present in an amount of 40 to 90 wt % based on the solution. In one aspect the carrier is present in an amount of 50 to 90 wt % based on the solution. In one aspect the carrier is present in an amount of 60 to 90 wt % based on the solution. In one aspect the carrier is present in an amount of 70 to 90 wt % based on the solution. In one aspect the carrier is present in an amount of 80 to 90 wt % based on the solution.

The nicotine solution may also comprise flavoring components. In this case the carrier may be propylene glycol. As used herein, the terms "flavor" and "flavorant" refer to materials which, where local regulations permit, may be used to create a desired taste or aroma in a product for adult consumers. They may include extracts (e.g. licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In one aspect the nicotine solution further comprises water. The water may be present in any suitable amount. In one aspect water is present in an amount of 1 to 50 wt % based on the solution. In one aspect water is present in an amount of 5 to 50 wt % based on the solution. In one aspect water is present in an amount of 10 to 50 wt % based on the solution. In one aspect water is present in an amount of 20 to 50 wt % based on the solution. In one aspect water is present in an amount of 1 to 40 wt % based on the solution. In one aspect water is present in an amount of 5 to 40 wt % based on the solution. In one aspect water is present in an amount of 10 to 40 wt % based on the solution. In one aspect water is present in an amount of 20 to 40 wt % based on the solution. In one aspect water is present in an amount of 1 to 30 wt % based on the solution. In one aspect water is present in an amount of 5 to 30 wt % based on the solution. In one aspect water is present in an amount of 10 to 30 wt % based on the solution. In one aspect water is present in an amount of 20 to 30 wt % based on the solution.

In one aspect the combined amount of carrier and water in the nicotine solution is from 1 to 98 wt % based on the solution. In one aspect the combined amount of carrier and water in the nicotine solution is 5 to 98 wt % based on the solution. In one aspect the combined amount of carrier and water in the nicotine solution is 10 to 98 wt % based on the solution. In one aspect the combined amount of carrier and water in the nicotine solution is 20 to 98 wt % based on the solution. In one aspect the combined amount of carrier and water in the nicotine solution is 30 to 98 wt % based on the solution. In one aspect the combined amount of carrier and water in the nicotine solution is 40 to 98 wt % based on the solution. In one aspect the combined amount of carrier and water in the nicotine solution is 50 to 98 wt % based on the solution. In one aspect the combined amount of carrier and water in the nicotine solution is 60 to 98 wt % based on the solution. In one aspect the combined amount of carrier and water in the nicotine solution is 70 to 98 wt % based on the solution. In one aspect the combined amount of carrier and water in the nicotine solution is 80 to 98 wt % based on the solution. In one aspect the combined amount of carrier and water in the nicotine solution is 90 to 98 wt % based on the solution. In one aspect the combined amount of carrier and water in the nicotine solution is 1 to 90 wt % based on the solution. In one aspect the combined amount of carrier and water in the nicotine solution is 5 to 90 wt % based on the solution. In one aspect the combined amount of carrier and water in the nicotine solution is 10 to 90 wt % based on the solution. In one aspect the combined amount of carrier and water in the nicotine solution is 20 to 90 wt % based on the solution. In one aspect the combined amount of carrier and water in the nicotine solution is 30 to 90 wt % based on the solution. In one aspect the combined amount of carrier and water in the nicotine solution is 40 to 90 wt % based on the solution. In one aspect the combined amount of carrier and water in the nicotine solution is 50 to 90 wt % based on the solution. In one aspect the combined amount of carrier and water in the nicotine solution is 60 to 90 wt % based on the solution. In one aspect the combined amount of carrier and water in the nicotine solution is 70 to 90 wt % based on the solution. In one aspect the combined amount of carrier and water in the nicotine solution is 80 to 90 wt % based on the solution. In one aspect the combined amount of carrier and water in the nicotine solution is 90 to 90 wt % based on the solution.

In one aspect the nicotine solution may contain solvents which advantageously allow for the preparation of the formulation. In one aspect, the nicotine solution contains ethanol which improves the solubility of benzoic acid when incorporated into the formulation.

The components of the system may be present in the following amounts. The water may represent up to 30% w/w of the total solution. The carrier may represent up to 98% w/w of the total solution. The nicotine may represent from greater than 0% to 6% w/w of the total solution.

In the context of the present disclosure, reference to a nicotine solution comprising nicotine in both protonated form and in unprotonated form generally means that the amount of nicotine in unprotonated form is not minimal. For example, the amount of non-protonated nicotine is typically greater than 1% w/w.

The nicotine solution comprises nicotine in unprotonated form and nicotine in protonated form. In one aspect the nicotine solution comprises nicotine in unprotonated form and nicotine in monoprotonated form. Although it is envisaged that the solution will typically comprise nicotine in unprotonated form and nicotine in monoprotonated form, it may be that small amounts of diprotonated nicotine are present. In one aspect the nicotine solution comprises nicotine in unprotonated form, nicotine in monoprotonated form and nicotine in diprotonated form.

As discussed herein, we have found that by protonating a portion of the nicotine and only a portion of the nicotine the desirable characteristics are observed. In one aspect from 1 to 80 wt % of the nicotine present in the solution is in protonated form. In one aspect from 2 to 80 wt % of the nicotine present in the solution is in protonated form. In one aspect from 3 to 80 wt % of the nicotine present in the solution is in protonated form. In one aspect from 4 to 80 wt % of the nicotine present in the solution is in protonated form. In one aspect from 5 to 80 wt % of the nicotine present in the solution is in protonated form. In one aspect from 10 to 80 wt % of the nicotine present in the solution is in protonated form. In one aspect from 15 to 80 wt % of the nicotine present in the solution is in protonated form. In one aspect from 20 to 80 wt % of the nicotine present in the solution is in protonated form. In one aspect from 25 to 80 wt % of the nicotine present in the solution is in protonated form. In one aspect from 30 to 80 wt % of the nicotine present in the solution is in protonated form. In one aspect from 35 to 80 wt % of the nicotine present in the solution is in protonated form. In one aspect from 40 to 80 wt % of the nicotine present in the solution is in protonated form. In one aspect from 45 to 80 wt % of the nicotine present in the solution is in protonated form. In one aspect from 50 to 80 wt % of the nicotine present in the solution is in protonated form. In one aspect from 55 to 80 wt % of the nicotine present in the solution is in protonated form.

In one aspect from 5 to 80 wt % of the nicotine present in the solution is in protonated form. In one aspect from 5 to 75 wt % of the nicotine present in the solution is in protonated form. In one aspect from 5 to 70 wt % of the nicotine present in the solution is in protonated form. In one aspect from 5 to 65 wt % of the nicotine present in the solution is in protonated form. In one aspect from 5 to 60 wt % of the nicotine present in the solution is in protonated form. In one aspect from 5 to 55 wt % of the nicotine present in the solution is in protonated form. In one aspect from 5 to 50 wt % of the nicotine present in the solution is in protonated form. In one aspect from 5 to 45 wt % of the nicotine present in the solution is in protonated form. In one aspect from 5 to 40 wt % of the nicotine present in the solution is in protonated form. In one aspect from 5 to 35 wt % of the nicotine present in the solution is in protonated form. In one aspect from 5 to 30 wt % of the nicotine present in the solution is in protonated form. In one aspect from 5 to 25 wt % of the nicotine present in the solution is in protonated form. In one aspect from 5 to 20 wt % of the nicotine present in the solution is in protonated form. In one aspect from 5 to 15 wt % of the nicotine present in the solution is in protonated form. In one aspect from 5 to 10 wt % of the nicotine present in the solution is in protonated form.

The relevant amounts of nicotine which are present in the solution in protonated form are specified herein. These amounts may be readily calculated by one skilled in the art. Nicotine, 3-(1-methylpyrrolidin-2-yl) pyridine, is a diprotic base with pKa of 3.12 for the pyridine ring and 8.02 for the pyrrolidine ring It can exist in pH-dependent protonated (mono- and di-) and non-protonated (free base) forms which have different bioavailability.

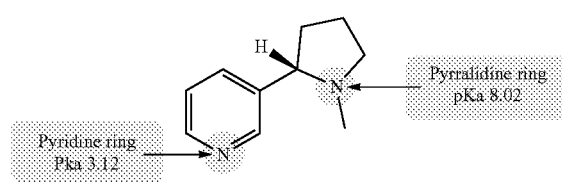

The distribution of protonated and non-protonated nicotine will vary at various pH increments.

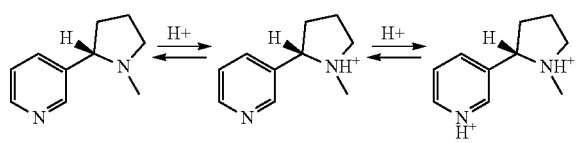

The fraction of non-protonated nicotine will be predominant at high pH levels whilst a decrease in the pH will see an increase of the fraction of protonated nicotine (mono- or di-depending on the pH). If the relative fraction of protonated nicotine and the total amount of nicotine in the sample are known, the absolute amount of protonated nicotine can be calculated.

The relative fraction of protonated nicotine in solution can be calculated by using the Henderson-Hasselbalch equation, which describes the pH as a derivation of the acid dissociation constant equation, and it is extensively employed in chemical and biological systems. Consider the following equilibrium:

$$B + H^+ \rightleftarrows BH^+$$

The Henderson-Hasselbalch equation for this equilibrium is:

$$pH = pKa + \log\frac{[B]}{[BH+]}$$

Where [B] is the amount of non-protonated nicotine (i.e. free base), [BH+] the amount of protonated nicotine (i.e. conjugate acid) and pKa is the reference pKa value for the pyrrolidine ring nitrogen of nicotine (pKa=8.02). The relative fraction of protonated nicotine can be derived from the alpha value of the non-protonated nicotine calculated from the Henderson-Hasselbalch equation as:

$$\% \text{ protonated nicotine} = 100 - \left\{ \frac{\frac{[B]}{[BH+]}}{\left\{1 + \frac{[B]}{[BH+]}\right\}} * 100 \right\}$$

Determination of pKa values of nicotine solutions was carried out using the basic approach described in "Spectroscopic investigations into the acid-base properties of nicotine at different temperatures", Peter M. Clayton, Carl A. Vas, Tam T. T. Bui, Alex F. Drake and Kevin McAdam, Anal. Methods, 2013, 5, 81-88.

As discussed herein the nicotine solution comprises nicotine in unprotonated form and nicotine in protonated form. As will be understood by one skilled in the art, the protonated form of nicotine is prepared by reacting unprotonated nicotine with an acid. The acids are one or more suitable acids, wherein at least benzoic acid, levulinic acid or a mixture thereof is present; and wherein the total content of acid present in the solution is no greater than 0.6 mole equivalents based on the nicotine. As is clear, at least benzoic acid, levulinic acid or a mixture thereof must be present. However, one or more acids in addition to the benzoic acid and/or levulinic acid may also be present. The presence of acids in addition to benzoic acid and levulinic acid is not excluded nor is it required. Thus in a further aspect, the present disclosure provides a nicotine solution comprising: (i) a carrier; (ii) nicotine in unprotonated form and in protonated form; and (iii) a first acid, wherein the first acid is selected from benzoic acid, levulinic acid and mixtures thereof; and (iv) an optional second acid, wherein the optional second acid, if present, is selected from acids other than benzoic acid, levulinic acid, and mixtures thereof; and wherein the total content of first acid and second acid present in the solution is no greater than 0.6 mole equivalents based on the nicotine.

The nicotine protonation may be provided in such a manner to achieve the desired degree of protonation of nicotine. In one aspect the optional second acid is an organic acid. In one aspect the optional second acid is a carboxylic acid. The carboxylic acid may be any suitable carboxylic acid. In one aspect the optional second acid is a mono-carboxylic acid.

In one aspect the optional second acid is selected from the group consisting of acetic acid, lactic acid, formic acid, citric acid, pyruvic acid, succinic acid, tartaric acid, oleic acid, sorbic acid, propionic acid, phenylacetic acid, and mixtures thereof.

In one aspect of the present disclosure, at least benzoic acid is present in the solution. In one aspect of the present disclosure, at least levulinic acid is present in the solution. In one aspect of the present disclosure, benzoic acid and levulinic acid are present in the solution.

As discussed herein the presence of acids in addition to benzoic acid and levulinic acid is not required. In one aspect, the presence of acids in addition to benzoic acid and levulinic acid is excluded. Thus in one aspect the nicotine solution contains acids selected from the group consisting of benzoic acid, levulinic acid and mixtures thereof. Thus in one aspect the present disclosure provides a nicotine solution comprising (i) a solvent; (ii) nicotine in unprotonated form and in protonated form; and (iii) acid selected from the group consisting of benzoic acid, levulinic acid and mixtures thereof; and wherein the total content of acid present in the solution is no greater than 0.6 mole equivalents based on the nicotine.

In one aspect benzoic acid is the only acid present. In one aspect the nicotine solution contains acid selected from the group consisting of benzoic acid.

In one aspect levulinic acid is the only acid present. In one aspect the nicotine solution contains acid selected from the group consisting of levulinic acid.

In one aspect benzoic acid and levulinic acid are the only acids present. In one aspect the nicotine solution contains acids selected from the group consisting of mixtures of benzoic acid and levulinic acid.

In one aspect the amount of levulinic acid present in the solution is less than 0.1 mole equivalents based on the nicotine. In one aspect the amount of levulinic acid present in the solution is no greater than 0.05 mole equivalents based on the nicotine. In one aspect the amount of levulinic acid present in the solution is no greater than 0.02 mole equivalents based on the nicotine. In one aspect the amount of levulinic acid present in the solution is no greater than 0.01 mole equivalents based on the nicotine. In one aspect the amount of levulinic acid present in the solution is no greater than 0.005 mole equivalents based on the nicotine. In one aspect the amount of levulinic acid present in the solution is no greater than 0.001 mole equivalents based on the nicotine. In one aspect the solution contain no levulinic acid.

The acids benzoic acid and levulinic acid are advantageous since we have found that on heating solutions containing benzoic acid and/or levulinic acid in an electronic vapor provision system the level of acid transfer to the aerosol is greater, with less production of degradation products compared to many other acids. Thus, we have found that the aerosol transfer for these acids is more efficient.

We have also found that benzoic acid provides a particularly desirable taste when the vaporized solution is inhaled. Thus in contrast to acids such as lactic acid, acetic acid and succinic acid, benzoic acid provides both good flavor and/or improved aerosol transfer efficiency. Thus, as disclosed herein in one aspect of the present disclosure, at least benzoic acid is present in the solution. Indeed when benzoic acid is present, the total limit on acid content described herein need not be observed. Thus in a further broad aspect the present disclosure provides a nicotine solution comprising: (i) a carrier; (ii) nicotine in protonated form and in unprotonated form; and (iii) benzoic acid.

In one aspect when benzoic acid is present, the nicotine solution contains no greater than 0.1 mole equivalents based on the nicotine of each of lactic acid, acetic acid and succinic acid. In one aspect the nicotine solution contains no greater than 0.01 mole equivalents based on the nicotine of each of lactic acid, acetic acid and succinic acid. Each of the preferred aspects of the present disclosure is equally applicable to this broad aspect of the disclosure.

The total content of acid present in the solution is no greater than 0.6 mole equivalents based on the nicotine. In one aspect the total content of acid present in the solution is no greater than 0.55 mole equivalents based on the nicotine. In one aspect the total content of acid present in the solution is no greater than 0.5 mole equivalents based on the nicotine. In one aspect the total content of acid present in the solution is no greater than 0.45 mole equivalents based on the nicotine. In one aspect the total content of acid present in the solution is no greater than 0.4 mole equivalents based on the nicotine. In one aspect the total content of acid present in the solution is no greater than 0.35 mole equivalents based on the nicotine. In one aspect the total content of acid present in the solution is no greater than 0.3 mole equivalents based on the nicotine.

In one aspect the combined amount of benzoic acid and levulinic acid present in the solution is no greater than 0.6 mole equivalents based on the nicotine. In one aspect the combined amount of benzoic acid and levulinic acid present in the solution is no greater than 0.55 mole equivalents based on the nicotine. In one aspect the combined amount of benzoic acid and levulinic acid present in the solution is no greater than 0.5 mole equivalents based on the nicotine. In one aspect the combined amount of benzoic acid and levulinic acid present in the solution is no greater than 0.45 mole equivalents based on the nicotine. In one aspect the combined amount of benzoic acid and levulinic acid present in the solution is no greater than 0.4 mole equivalents based on the nicotine. In one aspect the combined amount of benzoic acid and levulinic acid present in the solution is no greater than 0.35 mole equivalents based on the nicotine. In one aspect the combined amount of benzoic acid and levulinic acid present in the solution is no greater than 0.3 mole equivalents based on the nicotine.

The amount of benzoic acid present in the solution is no greater than 0.6 mole equivalents based on the nicotine. In one aspect the amount of benzoic acid present in the solution is no greater than 0.55 mole equivalents based on the nicotine. In one aspect the amount of benzoic acid present in the solution is no greater than 0.5 mole equivalents based on the nicotine. In one aspect the amount of benzoic acid present in the solution is no greater than 0.45 mole equivalents based on the nicotine. In one aspect the amount of benzoic acid present in the solution is no greater than 0.4 mole equivalents based on the nicotine. In one aspect the amount of benzoic acid present in the solution is no greater than 0.35 mole equivalents based on the nicotine. In one aspect the amount of benzoic acid present in the solution is no greater than 0.3 mole equivalents based on the nicotine. In each of these aspects, preferably benzoic acid is the only acid present and the nicotine solution contains acid selected from the group consisting of benzoic acid.

In one aspect the total content of acid present in the solution is no less than 0.01 mole equivalents based on the nicotine. In one aspect the total content of acid present in the solution is no less than 0.05 mole equivalents based on the nicotine. In one aspect the total content of acid present in the solution is no less than 0.1 mole equivalents based on the nicotine. In one aspect the total content of acid present in the solution is no less than 0.15 mole equivalents based on the nicotine. In one aspect the total content of acid present in the solution is no less than 0.2 mole equivalents based on the nicotine. In one aspect the total content of acid present in the solution is no less than 0.25 mole equivalents based on the nicotine. In one aspect the total content of acid present in the solution is no less than 0.3 mole equivalents based on the nicotine. In one aspect the total content of acid present in the solution is no less than 0.35 mole equivalents based on the nicotine. In one aspect the total content of acid present in the solution is no less than 0.4 mole equivalents based on the nicotine.

In one aspect the combined amount of benzoic acid and levulinic acid present in the solution is no less than 0.01 mole equivalents based on the nicotine. In one aspect the combined amount of benzoic acid and levulinic acid present in the solution is no less than 0.05 mole equivalents based on the nicotine. In one aspect the combined amount of benzoic acid and levulinic acid present in the solution is no less than 0.1 mole equivalents based on the nicotine. In one aspect the combined amount of benzoic acid and levulinic acid present in the solution is no less than 0.15 mole equivalents based on the nicotine. In one aspect the combined amount of benzoic acid and levulinic acid present in the solution is no less than 0.2 mole equivalents based on the nicotine. In one aspect the combined amount of benzoic acid and levulinic acid present in the solution is no less than 0.25 mole equivalents based on the nicotine. In one aspect the combined amount of benzoic acid and levulinic acid present in the solution is no less than 0.3 mole equivalents based on the nicotine. In one aspect the combined amount of benzoic acid and levulinic acid present in the solution is no less than 0.35 mole equivalents based on the nicotine. In one aspect the combined amount of benzoic acid and levulinic acid present in the solution is no less than 0.4 mole equivalents based on the nicotine.

In one aspect the amount of benzoic acid present in the solution is no less than 0.01 mole equivalents based on the nicotine. In one aspect the amount of benzoic acid present in the solution is no less than 0.05 mole equivalents based on the nicotine. In one aspect the amount of benzoic acid present in the solution is no less than 0.1 mole equivalents based on the nicotine. In one aspect the amount of benzoic acid present in the solution is no less than 0.15 mole equivalents based on the nicotine. In one aspect the amount of benzoic acid present in the solution is no less than 0.2 mole equivalents based on the nicotine. In one aspect the amount of benzoic acid present in the solution is no less than 0.25 mole equivalents based on the nicotine. In one aspect the amount of benzoic acid present in the solution is no less than 0.3 mole equivalents based on the nicotine. In one aspect the amount of benzoic acid present in the solution is no less than 0.35 mole equivalents based on the nicotine. In one aspect the amount of benzoic acid present in the solution is no less than 0.4 mole equivalents based on the nicotine.

In one aspect the total content of acid present in the solution is from 0.1 to 0.6 mole equivalents based on the nicotine. In one aspect the total content of acid present in the solution is from 0.1 to 0.5 mole equivalents based on the nicotine. In one aspect the total content of acid present in the solution is from 0.2 to 0.6 mole equivalents based on the nicotine. In one aspect the total content of acid present in the solution is from 0.1 to 0.4 mole equivalents based on the nicotine. In one aspect the total content of acid present in the solution is from 0.3 to 0.6 mole equivalents based on the nicotine. In one aspect the total content of acid present in the solution is from 0.2 to 0.5 mole equivalents based on the nicotine. In one aspect the total content of acid present in the solution is from 0.3 to 0.5 mole equivalents based on the nicotine. In one aspect the total content of acid present in the solution is from 0.2 to 0.4 mole equivalents based on the nicotine.

In one aspect the combined amount of benzoic acid and levulinic acid present in the solution is from 0.1 to 0.6 mole equivalents based on the nicotine. In one aspect the combined amount of benzoic acid and levulinic acid present in the solution is from 0.1 to 0.5 mole equivalents based on the nicotine. In one aspect the combined amount of benzoic acid and levulinic acid present in the solution is from 0.2 to 0.6 mole equivalents based on the nicotine. In one aspect the combined amount of benzoic acid and levulinic acid present in the solution is from 0.1 to 0.4 mole equivalents based on the nicotine. In one aspect the combined amount of benzoic acid and levulinic acid present in the solution is from 0.3 to 0.6 mole equivalents based on the nicotine. In one aspect the combined amount of benzoic acid and levulinic acid present in the solution is from 0.2 to 0.5 mole equivalents based on the nicotine. In one aspect the combined amount of benzoic acid and levulinic acid present in the solution is from 0.3 to 0.5 mole equivalents based on the nicotine. In one aspect the combined amount of benzoic acid and levulinic acid present in the solution is from 0.2 to 0.4 mole equivalents based on the nicotine.

In one aspect the amount of benzoic acid present in the solution is from 0.1 to 0.6 mole equivalents based on the nicotine. In one aspect the amount of benzoic acid present in the solution is from 0.1 to 0.5 mole equivalents based on the nicotine. In one aspect the amount of benzoic acid present in the solution is from 0.2 to 0.6 mole equivalents based on the nicotine. In one aspect the amount of benzoic acid present in the solution is from 0.1 to 0.4 mole equivalents based on the nicotine. In one aspect the amount of benzoic acid present in the solution is from 0.3 to 0.6 mole equivalents based on the nicotine. In one aspect the amount of benzoic acid present in the solution is from 0.2 to 0.5 mole equivalents based on the nicotine. In one aspect the amount of benzoic acid present in the solution is from 0.3 to 0.5 mole equivalents based on the nicotine. In one aspect the amount of benzoic acid present in the solution is from 0.2 to 0.4 mole equivalents based on the nicotine. In each of these aspects, preferably benzoic acid is the only acid present and the nicotine solution contains acid selected from the group consisting of benzoic acid.

As discussed herein we have found that at levels of acid addition required by the present invention, namely wherein the total content of acid present in the solution is no greater than 0.6 mole equivalents based on the nicotine, may be used across a broad range of nicotine content solutions. Nicotine solutions may be provided having desirable properties of flavor, impact, irritation, smoothness and/or nicotine reward for the user both when the nicotine content is relatively low, such as 1.9 wt % or 1.8 wt % nicotine or less and when the nicotine content is relatively high, such as greater than 1.9 wt % or 1.8 wt % nicotine. Thus in one aspect the nicotine solution comprises nicotine in an amount of no greater than 1.9 wt % or 1.8 wt % based on the total weight of the solution. Thus in one aspect the nicotine solution comprises nicotine in an amount of greater than 1.9 wt % or 1.8 wt % based on the total weight of the solution.

Nicotine may be provided at any suitable amount depending on the desired dosage when inhaled by the user. In one aspect nicotine is present in an amount of no greater than 6 wt % based on the total weight of the solution. In one aspect nicotine is present in an amount of from 0.4 to 6 wt % based on the total weight of the solution. In one aspect nicotine is present in an amount of from 0.8 to 6 wt % based on the total weight of the solution. In one aspect nicotine is present in an amount of from 1 to 6 wt % based on the total weight of the solution. In one aspect nicotine is present in an amount of from 1.8 to 6 wt % based on the total weight of the solution. In one aspect nicotine is present in an amount of from 0.4 to 5 wt % based on the total weight of the solution. In one aspect nicotine is present in an amount of from 0.8 to 5 wt % based on the total weight of the solution. In one aspect nicotine is present in an amount of from 1 to 5 wt % based on the total weight of the solution. In one aspect nicotine is present in an amount of from 1.8 to 5 wt % based on the total weight of the solution. In one aspect nicotine is present in an amount of no greater than 4 wt % based on the total weight of the solution. In one aspect nicotine is present in an amount of from 0.4 to 4 wt % based on the total weight of the solution. In one aspect nicotine is present in an amount of from 0.8 to 4 wt % based on the total weight of the solution. In one aspect nicotine is present in an amount of from 1 to 4 wt % based on the total weight of the solution. In one aspect nicotine is present in an amount of from 1.8 to 4 wt % based on the total weight of the solution. In one aspect nicotine is present in an amount of no greater than 3 wt % based on the total weight of the solution. In one aspect nicotine is present in an amount of from 0.4 to 3 wt % based on the total weight of the solution. In one aspect nicotine is present in an amount of from 0.8 to 3 wt % based on the total weight of the solution. In one aspect nicotine is present in an amount of from 1 to 3 wt % based on the total weight of the solution. In one aspect nicotine is present in an amount of from 1.8 to 3 wt % based on the total weight of the solution. In one aspect nicotine is present in an amount of no greater than 1.9 wt % based on the total weight of the solution. In one aspect nicotine is present in an amount of no greater than 1.8 wt % based on the total weight of the solution. In one aspect nicotine is present in an amount of from 0.4 to 1.9 wt % based on the total weight of the solution. In one aspect nicotine is present in an amount of from 0.4 to 1.8 wt % based on the total weight of the solution. In one aspect nicotine is present in an amount of from 0.5 to 1.9 wt % based on the total weight of the solution. In one aspect nicotine is present in an amount of from 0.5 to 1.8 wt % based on the total weight of the solution In one aspect nicotine is present in an amount of from 0.8 to 1.9 wt % based on the total weight of the solution. In one aspect nicotine is present in an amount of from 0.8 to 1.8 wt % based on the total weight of the solution. In one aspect nicotine is present in an amount of from 1 to 1.9 wt % based on the total weight of the solution. In one aspect nicotine is present in an amount of from 1 to 1.8 wt % based on the total weight of the solution. In one aspect nicotine is present in an amount of less than 1.9 wt % based on the total weight of the solution. In one aspect nicotine is present in an amount of less than 1.8 wt % based on the total weight of the solution. In one aspect nicotine is present in an amount of from 0.4 to less than 1.9 wt % based on the total weight of the solution. In one aspect nicotine is present in an amount of from 0.4 to less than 1.8 wt % based on the total weight of the solution. In one aspect nicotine is present in an amount of from 0.5 to less than 1.9 wt % based on the total weight of the solution. In one aspect nicotine is present in an amount of from 0.5 to less than 1.8 wt % based on the total weight of the solution. In one aspect nicotine is present in an amount of from 0.8 to less than 1.9 wt % based on the total weight of the solution. In one aspect nicotine is present in an amount of from 0.8 to less than 1.8 wt % based on the total weight of the solution. In one aspect nicotine is present in an amount of from 1 to less than 1.9 wt % based on the total weight of the solution. In one aspect nicotine is present in an amount of from 1 to less than 1.8 wt % based on the total weight of the solution.

In one aspect, when levulinic acid is present, nicotine is present in an amount of no greater than 1.9 wt % based on the total weight of the solution. In one aspect, when levulinic acid is present, nicotine is present in an amount of from 0.4 to 1.9 wt % based on the total weight of the solution. In one aspect, when levulinic acid is present, nicotine is present in an amount of from 0.5 to 1.9 wt % based on the total weight of the solution. In one aspect, when levulinic acid is present, nicotine is present in an amount of from 0.8 to 1.9 wt % based on the total weight of the solution. In one aspect, when levulinic acid is present, nicotine is present in an amount of from 1 to 1.9 wt % based on the total weight of the solution. In one aspect, when levulinic acid is present, nicotine is present in an amount of less than 1.9 wt % based on the total weight of the solution. In one aspect, when levulinic acid is present, nicotine is present in an amount of from 0.4 to less than 1.9 wt % based on the total weight of the solution. In one aspect, when levulinic acid is present, nicotine is present in an amount of from 0.5 to less than 1.9 wt % based on the total weight of the solution. In one aspect, when levulinic acid is present, nicotine is present in an amount of from 0.8 to less than 1.9 wt % based on the total weight of the solution. In one aspect, when levulinic acid is present, nicotine is present in an amount of from 1 to less than 1.9 wt % based on the total weight of the solution.

In one aspect, when levulinic acid is present, nicotine is present in an amount of no greater than 1.8 wt % based on the total weight of the solution. In one aspect, when levulinic acid is present, nicotine is present in an amount of from 0.4 to 1.8 wt % based on the total weight of the solution. In one aspect, when levulinic acid is present, nicotine is present in an amount of from 0.5 to 1.8 wt % based on the total weight of the solution. In one aspect, when levulinic acid is present, nicotine is present in an amount of from 0.8 to 1.8 wt % based on the total weight of the solution. In one aspect, when levulinic acid is present, nicotine is present in an amount of from 1 to 1.8 wt % based on the total weight of the solution. In one aspect, when levulinic acid is present, nicotine is present in an amount of less than 1.8 wt % based on the total weight of the solution. In one aspect, when levulinic acid is present, nicotine is present in an amount of from 0.4 to less than 1.8 wt % based on the total weight of the solution. In one aspect, when levulinic acid is present, nicotine is present in an amount of from 0.5 to less than 1.8 wt % based on the total weight of the solution. In one aspect, when levulinic acid is present, nicotine is present in an amount of from 0.8 to less than 1.8 wt % based on the total weight of the solution. In one aspect, when levulinic acid is present, nicotine is present in an amount of from 1 to less than 1.8 wt % based on the total weight of the solution.

In one aspect nicotine is present in an amount of less than 1.8 wt % and the acids present are only benzoic acid, levulinic acid or mixtures thereof. Thus in one aspect the present disclosure provides a nicotine solution comprising (i) a carrier; (ii) nicotine in unprotonated form and in protonated form, wherein nicotine is present in an amount of less than 1.8 wt % based on the total weight of the solution; and (iii) acid selected from the group consisting of benzoic acid, levulinic acid and mixtures thereof; and wherein the total content of acid present in the solution is no greater than 0.6 mole equivalents based on the nicotine. In this aspect the combined amount of benzoic acid and levulinic acid present in the solution may be from 0.1 to 0.6 mole equivalents based on the nicotine, such as from 0.1 to 0.5 mole equivalents based on the nicotine, such as from 0.2 to 0.6 mole equivalents based on the nicotine, such as from 0.1 to 0.4 mole equivalents based on the nicotine, such as from 0.3 to 0.6 mole equivalents based on the nicotine, such as from 0.2 to 0.5 mole equivalents based on the nicotine, such as from 0.3 to 0.5 mole equivalents based on the nicotine, such as from 0.2 to 0.4 mole equivalents based on the nicotine.

In one aspect nicotine is present in an amount of less than 1.9 wt % and the acids present are only benzoic acid. Thus in one aspect the present disclosure provides a nicotine solution comprising (i) a carrier; (ii) nicotine in unprotonated form and in protonated form, wherein nicotine is present in an amount of less than 1.9 wt % based on the total weight of the solution; and (iii) acid selected from the group consisting of benzoic acid; and wherein the total content of acid present in the solution is no greater than 0.6 mole equivalents based on the nicotine. In this aspect the amount of benzoic acid present in the solution may be from 0.1 to 0.6 mole equivalents based on the nicotine, such as from 0.1 to 0.5 mole equivalents based on the nicotine, such as from 0.2 to 0.6 mole equivalents based on the nicotine, such as from 0.1 to 0.4 mole equivalents based on the nicotine, such as from 0.3 to 0.6 mole equivalents based on the nicotine, such as from 0.2 to 0.5 mole equivalents based on the nicotine, such as from 0.3 to 0.5 mole equivalents based on the nicotine, such as from 0.2 to 0.4 mole equivalents based on the nicotine.

In one aspect nicotine is present in an amount of less than 1.8 wt % and the acids present are only benzoic acid. Thus in one aspect the present disclosure provides a nicotine solution comprising (i) a carrier; (ii) nicotine in unprotonated form and in protonated form, wherein nicotine is present in an amount of less than 1.8 wt % based on the total weight of the solution; and (iii) acid selected from the group consisting of benzoic acid; and wherein the total content of acid present in the solution is no greater than 0.6 mole equivalents based on the nicotine. In this aspect the amount of benzoic acid present in the solution may be from 0.1 to 0.6 mole equivalents based on the nicotine, such as from 0.1 to 0.5 mole equivalents based on the nicotine, such as from 0.2 to 0.6 mole equivalents based on the nicotine, such as from 0.1 to 0.4 mole equivalents based on the nicotine, such as from 0.3 to 0.6 mole equivalents based on the nicotine, such as from 0.2 to 0.5 mole equivalents based on the nicotine, such as from 0.3 to 0.5 mole equivalents based on the nicotine, such as from 0.2 to 0.4 mole equivalents based on the nicotine.

As will be understood by one skilled in the art, the present disclosure requires that the nicotine be partially protonated prior to vaporization. This protonation may occur at any time before vaporization. In one aspect the nicotine is partially protonated very shortly prior to vaporization. For example the nicotine may be partially protonated as part of the process to provide vaporization. Thus it is envisaged that an 'inline' process may be provided in which nicotine in unprotonated form is contacted with the desired acid and the partially protonated nicotine solution which is formed is then vaporized. It is also envisaged that the end user may be provided with the necessary acid and combine this with purchased nicotine in unprotonated form. The then partially protonated nicotine solution may then be used in an electronic vapor provision system in place of unprotonated nicotine. Thus in a further aspect there is provided a kit for a nicotine solution of the disclosure, the kit comprising (a) a nicotine solution comprising a carrier and nicotine in unprotonated form; and (b) one or more acids, wherein at least benzoic acid, levulinic acid or a mixture thereof is present; in separate packages or containers; with instructions for admixture and/or contacting and/or use to provide a partially protonated nicotine solution in which the total content of acid present in the solution is no greater than 0.6 mole equivalents based on the nicotine. In a further aspect there is also provided a process for improving the sensory properties of a vaporized nicotine solution, the process comprising: (a) providing a nicotine solution comprising (i) a carrier; and (ii) nicotine in unprotonated form; and (b) providing an acid solution comprising one or more acids, wherein at least benzoic acid, levulinic acid or a mixture thereof is present; (c) vaporizing the nicotine solution and the acid solution; and (d) combining the vaporized nicotine solution and the vaporized acid solution, such that the acid is present in an amount of no greater than 0.6 mole equivalents based on the nicotine.

The solution may be contained or delivered by any means. In one aspect the present disclosure provides a contained nicotine solution comprising (a) a container; and (b) a nicotine solution, comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine. The container may be any suitable container, for example to allow for the storage or delivery of the solution. In one aspect the container is configured for engagement with an electronic vapor provision system. The container may be configured to become fluidly in communication with an electronic vapor provision system so that solution may be delivered to the electronic vapor provision system. As described above, the present disclosure relates to container which may be used in an electronic vapor provision system, such as an e-cigarette. Throughout the following description the term "e-cigarette" is used; however, this term may be used interchangeably with electronic vapor provision system.

As discussed herein, the container of the present disclosure is typically provided for the delivery of nicotine solution to or within an e-cigarette. The nicotine solution may be held within an e-cigarette or may be sold as a separate container for subsequent use with or in an e-cigarette. As understood by one skilled in the art, e-cigarettes may contain a unit known as a detachable cartomizer which typically comprises a reservoir of nicotine solution, a wick material and a heating element for vaporizing the nicotine. In some e-cigarettes, the cartomizer is part of a single-piece device and is not detachable. In one aspect the container is a cartomizer or is part of a cartomizer. In one aspect the container is not a cartomizer or part of a cartomizer and is a container, such as a tank, which may be used to deliver nicotine solution to or within an e-cigarette.

In one aspect the container is part of an e-cigarette. Therefore in a further aspect the present disclosure provides an electronic vapor provision system comprising: a vaporizer for vaporizing liquid for inhalation by a user of the electronic vapor provision system; a power supply comprising a cell or battery for supplying power to the vaporizer a nicotine solution, comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine.

In addition to the solution of the present disclosure and to systems such as containers and electronic vapor provision systems containing the same, the present disclosure provides a process for improving the sensory properties of a vaporized nicotine solution. The process comprises: (a) providing a nicotine solution comprising (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine; (b) vaporizing the nicotine solution.

Reference to an improvement in the sensory properties of a vaporized nicotine solution refer may include an improvement in the smoothness of the vaporized nicotine solution as perceived by a user.

The process of the present disclosure may comprises additional steps either before the steps listed, after the steps listed or between one or more of the steps listed.

In addition to the solution of the present disclosure and to systems such as containers and electronic vapor provision systems containing the same, the present disclosure provides use of one or more acids for improving sensory properties of a vaporized nicotine solution. In the use the nicotine solution comprises (i) a carrier; (ii) nicotine in unprotonated form and in protonated form; and (iii) one or more acids, wherein at least benzoic acid, levulinic acid or a mixture thereof is present; and wherein the total content of acid present in the solution is no greater than 0.6 mole equivalents based on the nicotine.

BRIEF DESCRIPTION OF THE DRAWINGS

The present disclosure will now be described in further detail by way of example only with reference to the accompanying FIGURE in which:

FIG. 1 shows a graph illustrating variation of $p_sK_{a2}$ with nicotine concentration.

DETAILED DESCRIPTION

The invention will now be described with reference to the following non-limiting example.

EXAMPLES

Determination of pKa Values

The determination of pKa values of nicotine in glycerol/water systems was carried out using the basic approach described in "Spectroscopic investigations into the acid-base properties of nicotine at different temperatures", Peter M. Clayton, Carl A. Vas, Tam T. T. Bui, Alex F. Drake and Kevin McAdam, Anal. Methods, 2013, 5, 81-88, and summarized below. Because the system is predominately non-aqueous the parameter $p_sK_{a2}$ was measured, where subscript s refers to the solvent composition in this largely non-aqueous system, and subscript 2 refers to the $pK_a$ value of the pyrrolidyl nitrogen.

Further information on the determination of pKa values of nicotine is provided in "Use of chiroptical spectroscopy to determine the ionisation status of (S)-nicotine in e-cigarette formulations and snus", Clayton et al, ST 49, CORESTA Congress, Qubec City, Canada, 12-16 Oct. 2014 (available at http://www.bat-science.com/groupms/sites/BAT_9GVJXS.nsf/vwPagesWebLive/DO9PVC3 G/$FILE/CORE STA_PC_2014.pdf).

A range of glycerol/water/nicotine solutions were prepared, with the water concentration fixed at 9%, the nicotine concentration varying from 30 µg/ml to 3 mg/ml; and the glycerol content comprising the remainder of the solutions.

Simultaneous UV & CD spectra of glycerol/s-nicotine/water solutions were measured on the Applied Photophysics Ltd (Leatherhead, UK) Chiracsan Plus spectrometer. The UV absorbance & CD spectra were measured between 300-200 nm region, with various pathlengths depending upon the nicotine concentration of the solution—10 mm, 5 mm, 2 mm, 1 mm, 0.5 mm, 0.1 mm and 0.01 mm pathlengths. The instrument was flushed continuously with pure evaporated nitrogen throughout the measurements. Throughout measurements spectra were recorded with a 0.5 nm step size, a 1 s measurement time-per-point and a spectral bandwidth of 2 nm. Where possible, all CD spectra were smoothed with a window factor of 4 using the Savitzky-Golay method for better presentation.

Solutions of S-Nicotine in glycerol/water were pH titrated at 23° C. The pH of these solutions was raised towards alkaline by adding small aliquots of NaOH (~pH10) and then lowered to pH2 by adding small aliquots of HCl. A series of 0.1M, 0.5M, 1M, 5M and 10M of HCl and NaOH solutions were used during the pH titration. pHs were measured at 23° C. using a Corning pH105 pH meter with a RMS pH electrode. The $p_sK_{a2}$ values changed systematically with nicotine concentration (FIG. 1) and therefore values for $p_sK_{a2}$ were calculated at each nicotine concentration level (Table 1). Due to the viscosity of the solutions, and the optical density in the CD spectra of the high nicotine concentration solutions, very small path-length cells were required for nicotine concentrations above 3 mg/ml. Satisfactory sample preparation and spectroscopy could not be achieved with the necessary small cells at these concentrations, and therefore the $p_sK_{a2}$ at higher concentrations were calculated from a regression fit to FIG. 1.

TABLE 1

$p_sK_{a2}$ values measured at various nicotine concentrations in a 9% water, nicotine/glycerol system.

| $p_sK_{a2}$ | conc (g/L) | conc (mM) | $\log_{10}$ [conc] |
|---|---|---|---|
| 7.49 | 0.03 | 0.185 | −0.732 |
| 7.34 | 0.06 | 0.370 | −0.431 |
| 7.30 | 0.3 | 1.85 | 0.268 |
| 7.27 | 0.6 | 3.70 | 0.569 |
| 7.25 | 3 | 18.53 | 1.268 |

Curve fitting, using the equation $y=0.0233e^{((\log_{10}[nicotine]/0.325)}+7.26$ provided a $p_sK_{a2}$ value of 7.26 at 30 mg/ml nicotine concentration. Use of this $p_sK_{a2}$ value with the Henderson-Hasselbalch equation allows calculation of the degree of nicotine protonation at any pH value.

Example 1

A series of tests were conducted using Vype E-pen electronic cigarettes. The "unprotonated nicotine control" devices were loaded with solution containing 1.86% (w/w) nicotine, 25% propylene glycol containing tobacco flavor "A", 25% water and 48.1% glycerol. A pH of 8.7 was measured for this solution, indicating 4% protonation of nicotine.

A similar set of devices were prepared wherein 0.55% w/w (0.4 Meq to nicotine) benzoic acid was added to the formulation, with the glycerol content was commensurately reduced to 47.6% (w/w). A pH of 7.4 was measured for this solution, indicating 43% protonation of nicotine.

A third set of devices were prepared wherein 0.25% w/w (0.2 Meq to nicotine) benzoic acid was added to the formulation, with the glycerol content was commensurately adjusted to 47.9% (w/w). A pH of 7.8 was measured for this solution, indicating 24% protonation of nicotine.

One each of these e-cigarettes was presented to 15 panelists comprising e-cigarette users, and the panelists were asked to puff on the e-cigarettes in a sequential monadic fashion for 10 puffs on each device. They were asked to identify the preferred e-cigarette from the three offered to them.

7 panelists preferred the unprotonated control e-cigarette, and 8 people preferred the acidified samples—4 preferred the 0.2 Meq device and 4 preferred the 0.4 Meq device.

Example 2

A series of tests were conducted using Vype E-pen electronic cigarettes. The "unprotonated nicotine control" devices were loaded with solution containing 1.86% (w/w) nicotine, 35.3% propylene glycol containing mint flavor, 25% water and 37.9 glycerol. This solution had a pH of 9.7 indicating <1% nicotine protonation.

A similar set of devices were prepared wherein 0.55% w/w (0.4 Meq to nicotine) benzoic acid was added to the formulation, with the glycerol content was commensurately reduced to 37.3% (w/w). This solution had a pH of 7.4 indicating nicotine protonation of 43%.

A third set of devices were prepared wherein 0.25% w/w (0.2 Meq to nicotine) benzoic acid was added to the formulation, with the glycerol content was commensurately adjusted to 37.6% (w/w). This solution had a pH of 7.8 indicating nicotine protonation of 22%.

One each of these e-cigarettes was presented to 15 panelists comprising e-cigarette users, and the panelists were asked to puff on the e-cigarettes in a sequential monadic fashion for 10 puffs on each device. They were asked to identify the preferred e-cigarette from the three offered to them.

4 panelists preferred the unprotonated control e-cigarette, and 11 people preferred the acidified samples—2 preferred the 0.2 Meq device and 9 preferred the 0.4 Meq device.

Example 3

A series of tests were conducted using Vype E-pen electronic cigarettes. The "unprotonated nicotine control" devices were loaded with solution containing 1.86% (w/w) nicotine, 25% propylene glycol containing a cherry flavor, 25% water and 48.1% glycerol. This solution had a pH of 8.4 indicating nicotine protonation at a level of 7%.

A similar set of devices were prepared wherein 0.55% w/w (0.4 Meq to nicotine) benzoic acid was added to the formulation, with the glycerol content was commensurately reduced to 47.6% (w/w). This solution had a pH of 7.4 indicating nicotine protonation at a level of 43%.

A third set of devices were prepared wherein 0.25% w/w (0.2 Meq to nicotine) benzoic acid was added to the formulation, with the glycerol content was commensurately adjusted to 47.9% (w/w). This solution had a pH of 7.8 indicating nicotine protonation at a level of 24%

One each of these e-cigarettes was presented to 15 panelists comprising e-cigarette users, and the panelists were asked to puff on the e-cigarettes in a sequential monadic fashion for 10 puffs on each device. They were asked to identify the preferred e-cigarette from the three offered to them. 3 panelists preferred the unprotonated control e-cigarette, and 12 people preferred the acidified samples—8 preferred the 0.2 Meq device and 4 preferred the 0.4 Meq device.

Example 4

A series of tests were conducted using Vype E-pen electronic cigarettes. The "unprotonated nicotine control" devices were loaded with solution containing 1.86% (w/w) nicotine, 25% propylene glycol containing tobacco flavor "A", 25% water and 48.1% glycerol. This solution had a pH of 8.6 indicating nicotine protonation at a level of 4%.

A similar set of devices were prepared wherein 0.41% w/w (0.3 Meq to nicotine) benzoic acid was added to the formulation, with the glycerol content was commensurately reduced to 47.7% (w/w). This solution had a pH of 7.7 indicating nicotine protonation at a level of 26%.

A third set of devices were prepared wherein 0.39% w/w (0.3 Meq to nicotine) levulinic acid was added to the formulation, with the glycerol content was commensurately adjusted to 47.8% (w/w). This solution had a pH of 7.26 indicating nicotine protonation at a level of 50%.

One each of these e-cigarettes was presented to 14 panelists comprising e-cigarette users, and the panelists were asked to puff on the e-cigarettes in a sequential monadic fashion for 10 puffs on each device. They were asked to identify the preferred e-cigarette from the three offered to them.

3 panelists preferred the unprotonated control e-cigarette, and 11 people preferred the acidified samples—7 preferred the 0.3 Meq benzoic acid device and 4 preferred the 0.3 Meq levulinic acid device.

Example 5

A series of tests were conducted using Vype E-pen electronic cigarettes. The "unprotonated nicotine control" devices were loaded with solution containing 1.8% (w/w) nicotine, 25% propylene glycol containing tobacco flavor "B", 25% water and 48.1% glycerol. This solution had a pH of 9.3 indicating nicotine protonation at a level of 1%.

A similar set of devices were prepared wherein 0.41% w/w (0.3 Meq to nicotine) benzoic acid was added to the formulation, with the glycerol content was commensurately reduced to 47.7% (w/w). This solution had a pH of 7.7 indicating nicotine protonation at a level of 28%.

A third set of devices were prepared wherein 0.39% w/w (0.3 Meq to nicotine) levulinic acid was added to the formulation, with the glycerol content was commensurately adjusted to 47.8% (w/w). This solution had a pH of 7.4 indicating nicotine protonation at a level of 41%.

One each of these e-cigarettes was presented to 11 panelists comprising e-cigarette users, and the panelists were asked to puff on the e-cigarettes in a sequential monadic fashion for 10 puffs on each device. They were asked to identify the preferred e-cigarette from the three offered to them.

4 panelists preferred the unprotonated control e-cigarette, and 7 people preferred the acidified samples—4 preferred the 0.3 Meq benzoic acid device and 3 preferred the 0.3 Meq levulinic acid device.

Example 6

A series of tests were conducted using Vype E-stick electronic cigarettes. The "unprotonated nicotine control" devices were loaded with solution containing 4% (w/w) nicotine, 25% propylene glycol containing a cherry flavor, 9% water and 62% glycerol. This solution had a pH of 8.3 indicating nicotine protonation at a level of 7%.

A similar set of devices were prepared wherein 1.2% w/w (0.4 Meq to nicotine) benzoic acid was added to the formulation, with the glycerol content was commensurately reduced to 60.8% (w/w). This solution had a pH of 7.4 indicating nicotine protonation at a level of 41%.

A third set of devices were prepared wherein 1.15% w/w (0.4 Meq to nicotine) levulinic acid was added to the formulation, with the glycerol content was commensurately adjusted to 60.9% (w/w). This solution had a pH of 6.9 indicating nicotine protonation at a level of 68%.

One each of these e-cigarettes was presented to 11 panelists comprising e-cigarette users, and the panelists were asked to puff on the e-cigarettes in a sequential monadic fashion for 10 puffs on each device. They were asked to identify the preferred e-cigarette from the three offered to them.

1 panelist preferred the unprotonated control e-cigarette, and 10 people preferred the acidified samples—6 preferred the 0.4 Meq benzoic acid device and 4 preferred the 0.4 Meq levulinic acid device.

Example 7

A series of tests were conducted using Vype E-stick electronic cigarettes. The "unprotonated nicotine control" devices were loaded with solution containing 4% (w/w) nicotine, 36.5% propylene glycol containing a mint flavor, 9% water and 50.5% glycerol. This solution had a pH of 9.6 indicating nicotine protonation at a level of <1%.

A similar set of devices were prepared wherein 1.2% w/w (0.4 Meq to nicotine) benzoic acid was added to the formulation, with the glycerol content was commensurately reduced to 49.3% (w/w). This solution had a pH of 7.3 indicating nicotine protonation at a level of 51%.

A third set of devices were prepared wherein 1.15% w/w (0.4 Meq to nicotine) levulinic acid was added to the formulation, with the glycerol content was commensurately adjusted to 49.35% (w/w). This solution had a pH of 6.8 indicating nicotine protonation at a level of 73%.

One each of these e-cigarettes was presented to 11 panelists comprising e-cigarette users, and the panelists were asked to puff on the e-cigarettes in a sequential monadic fashion for 10 puffs on each device. They were asked to identify the preferred e-cigarette from the three offered to them.

2 panelists preferred the unprotonated control e-cigarette, and 9 people preferred the acidified samples—5 preferred the 0.4 Meq benzoic acid device and 4 preferred the 0.4 Meq levulinic acid device.

Example 8

A series of tests were conducted using Vype E-pen electronic cigarettes. The devices were loaded with the following solutions:

A—1.86% w/w nicotine, 0.42% w/w benzoic acid (~0.3 Meq to nicotine), 47.72% w/w glycerol, 25% w/w water, 19.5% w/w propylene glycol and 5.5% w/w flavor B—1.86% w/w nicotine, 0.42% w/w benzoic acid (~0.3 Meq to nicotine), 47.72% w/w glycerol, 25% w/w water, 13% w/w propylene glycol and 12% w/w flavor C—1.86% w/w nicotine, 0.42% w/w benzoic acid (~0.3 Meq to nicotine), 37.22% w/w glycerol, 25% w/w water, 30% w/w propylene glycol and 5.5% w/w flavor Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A cartomizer containing a nicotine solution and a heating element, the nicotine solution comprising:
   (i) a carrier;
   (ii) nicotine in unprotonated form and in protonated form, wherein nicotine is present in an amount of from 1.8 to 6 wt% based on the total weight of the solution; and
   (iii) an acid selected from the group consisting of benzoic acid; and
   wherein the total content of acid present in the solution is between 0.3 and 0.6 mole equivalents based on the nicotine.

2. The cartomizer according to claim 1 wherein the nicotine solution further comprises water.

3. The cartomizer according to claim 1 comprising nicotine in an amount of no greater than 2 wt% based on the total weight of the nicotine solution.

4. The cartomizer according to claim 1 wherein the carrier is a solvent.

5. The cartomizer according to claim 4 wherein the solvent is selected from glycerol, propylene glycol and mixtures thereof.

* * * * *